United States Patent
Sanchez et al.

(10) Patent No.: US 8,323,986 B2
(45) Date of Patent: Dec. 4, 2012

(54) MOLECULAR ASSEMBLY ON A SUBSTRATE

(75) Inventors: Javier Sanchez, Spånga (SE); Rolf Larsson, Uppsala (SE)

(73) Assignee: Corline Systems AB, Uppsala (SE)

( * ) Notice: Subject to any disclaimer, the term of this patent is extended or adjusted under 35 U.S.C. 154(b) by 576 days.

(21) Appl. No.: 12/444,546

(22) PCT Filed: Sep. 28, 2007

(86) PCT No.: PCT/SE2007/050685
§ 371 (c)(1),
(2), (4) Date: Mar. 8, 2010

(87) PCT Pub. No.: WO2008/041930
PCT Pub. Date: Apr. 10, 2008

(65) Prior Publication Data
US 2010/0178657 A1    Jul. 15, 2010

(30) Foreign Application Priority Data
Oct. 6, 2006   (SE) ...................................... 0602120

(51) Int. Cl.
*G01N 33/551*   (2006.01)
(52) U.S. Cl. ...... 436/518; 436/524; 435/7.1; 435/283.1; 435/287.1; 422/50; 422/430; 422/68.1
(58) Field of Classification Search ................. 436/518, 436/524; 435/7.1, 283.1, 287.1; 422/50, 422/430, 68.1
See application file for complete search history.

(56) References Cited

U.S. PATENT DOCUMENTS

| 5,529,986 A | 6/1996 | Larsson et al. |
| 5,773,224 A * | 6/1998 | Grandics et al. ............... 435/7.2 |
| 2003/0129130 A1 | 7/2003 | Guire et al. |

FOREIGN PATENT DOCUMENTS

| WO | 9305793 A1 | 4/1993 |
| WO | 0040253 A1 | 7/2000 |
| WO | 0045837 A1 | 8/2000 |

OTHER PUBLICATIONS

Kett et al., Avidin is a heparain-binding protein. Affinity, specificity and structural analysis, 2003, Biochimica et Biophisica Acta, vol. 1620, pp. 225-234.*
Tseng, et al.,"Fabrication and Characterization of Heparin Fuctionalized Membrane-Mimetic Assemblies," Biomaterials, 2006, pp. 2627-2636, vol. 27.
Blum-Ricard, et al.,"Dual Polarization Interferometry Characterization of Carbohydrate-Protein Interactions," Analytical Biochemistry, 2006, pp. 252-259, vol. 352.

* cited by examiner

*Primary Examiner* — Melanie J Yu
(74) *Attorney, Agent, or Firm* — Browdy and Neimark, PLLC

(57) ABSTRACT

The present invention relates to a molecular assembly on a substrate usable for studying and/or performing biological interactions and/or reactions The invention further relates to an in vitro method to provide a substrate with a heparin coating presenting biotinylated biomolecules comprising linking avidin to a surface capable of binding avidin. A heparin conjugate is then linked to the avidin treated surface to form a layer of heparin thereon. Finally, a biotinylated biological probe or biomolecule is linked to the avidin through the layer of heparin thereby forming an essentially biologically inert surface with biotinylated probes extending out from the surface.

17 Claims, 2 Drawing Sheets

MOLECULAR ASSEMBLY ON A SUBSTRATE

FIELD OF THE INVENTION

The present invention relates to a molecular assembly on a substrate usable for studying and/or performing biological interactions and/or reactions, and to a method for providing such an assembly.

BACKGROUND OF THE INVENTION

The well-known high affinity reaction between biotin and streptavidin or avidin is a versatile tool in biomedicine. However, any substrate carrying streptavidin or avidin on its surface is trombogenic in contact with blood. Surfaces comprising streptavidin or avidin can also trigger other unwanted reactions in contact with other biological media. Therefore, such substrates are not suitable for applications intended to be in contact with blood or other biological media. Efforts on developing e.g. blood compatible surfaces have previously been described in the literature, with various results. However, so far no fully satisfactory means and methods have been devised.

PRIOR ART

The International patent application PCT/SE2006/050224 (Corline) discloses a method of producing a heparin surface wherein the last step comprises linkage of a high molecular weight heparin conjugate to an avidin treated surface. The method is based on the strong binding affinity between avidin and heparin. The strength is further increased by multiple linking sites present through the high molecular weight heparin conjugate. The purpose of the invention according to the above cited application is to provide biologically inert surfaces, suitable for use in i.e. transplantation of tissue, whereby the tissue in question is coated with said heparin conjugate.

The heparin conjugate as such is disclosed in the European patent EP0658112 (Corline).

SUMMARY OF THE INVENTION

Thus, there exists a need for improved carrier substrates for biomolecules so as to provide essentially biologically inert surfaces, which do not interfere with reactions and/or interactions between the immobilized biomolecules and other species of interest present in biological fluids of different kinds. Such substrates would be very suitable for modification of surfaces in general, both artificial, e.g. for use as biosensors, implants etc, as well as for protection and/or modification of biological tissue, e.g living cells.

The present inventors have surprisingly found that despite an adequate coverage of heparin on a layer of avidin, provided on a carrier substrate, for the purpose of preparing a non-thrombogenic heparin surface, as disclosed in '224 discussed above, the biotin binding sites of avidin have been shown not to be completely blocked by the heparin. Thus, there are still accessible binding sites for biotin on the avidin molecules, which may be used for adding biotinylated biological probes. These probes, suitably biomolecules, will thus become "anchored" in the heparin layer through the binding of biotin residues to the avidin, and will protrude from the heparin surface where they will be usable as probes for the desired interactions/reactions to be studied. The heparin layer will form an essentially "inert" layer in respect of the reactions that are of interest to study. The biological probes or biomolecules may also be used as target oriented probes for therapeutic purposes.

Preferably the biotinylated probes or biomolecules are selected from the group consisting of antibodies, fragments of antibodies, growth factors, regulators of complement, regulators of coagulation, anti-inflammatory agents, extracellular matrix proteins.

The present invention therefore in a first aspect relates to a molecular assembly on a substrate comprising an essentially biologically inert surface having biological probes anchored therein, and is defined in claim 1.

In a further aspect, the invention relates to a method comprising a stepwise procedure to obtain a heparin coating on a surface where addition of biotinylated biological probes or biomolecules to the surface by anchoring in the heparin layer is possible.

DETAILED DESCRIPTION OF THE INVENTION

For the purpose of this application the following definitions are given.

By "biotinylated biomolecules" is meant molecules and/or cells that are surface-modified by biotin. The term "substrate" means a surface or material suitable for binding avidin. The term "probe" means a chemical structure that probes, examines or tests. It has some kind of reactive site, capable of interacting with other species, preferably in solution.

"Essentially biologically inert" shall be taken to mean that there will be essentially no interfering/blocking interactions, such as e.g. blood clotting or cell depositions, between a surface which has been coated with an assembly according to the invention, and the fluid to which such surface is exposed, such that interactions between biomolecules anchored in said surface and the species of interest in the fluid can occur with the desired accuracy, and without disturbances.

A "heparin layer" shall be taken to mean a layer comprising heparin. Thus a heparin conjugate forming a layer will fall under this definition.

A prior art method of coating tissue and other substrates with heparin is disclosed in PCT/SE2006/050224, as mentioned in the Background section. The method comprises attaching a heparin conjugate to the substrate by means of an avidin linkage.

The present invention is based on the surprising discovery that avidin entities within such surfaces coated with heparin conjugate according to said prior art technique, despite providing adequate protection against undesired reactions such as thrombosis, still are accessible for binding via a biotin residue present on a biological probe. The substrate thus obtains a further feature of directed capturing reaction with a selected biomolecule (see the Examples).

Figure 1A:
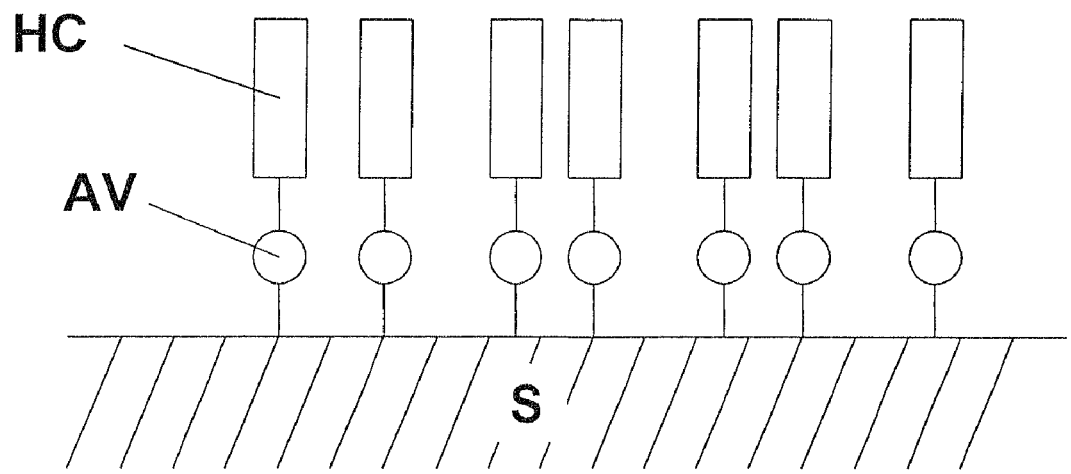
FIG. 1a schematically illustrates an assembly according to the prior art document PCT SE2006/050224.

FIG. 1a shows schematically a substrate coated with heparin according to '224, wherein a heparin conjugate HC is linked to the substrate S via avidin A. The HC is fully disclosed in the above cite EP 0658 112, and can be described as a macromolecular conjugate consisting of a carrier chain (PAV; a polymeric amine) to which approximately 70 heparin molecules are covalently linked.

Figure 1B:
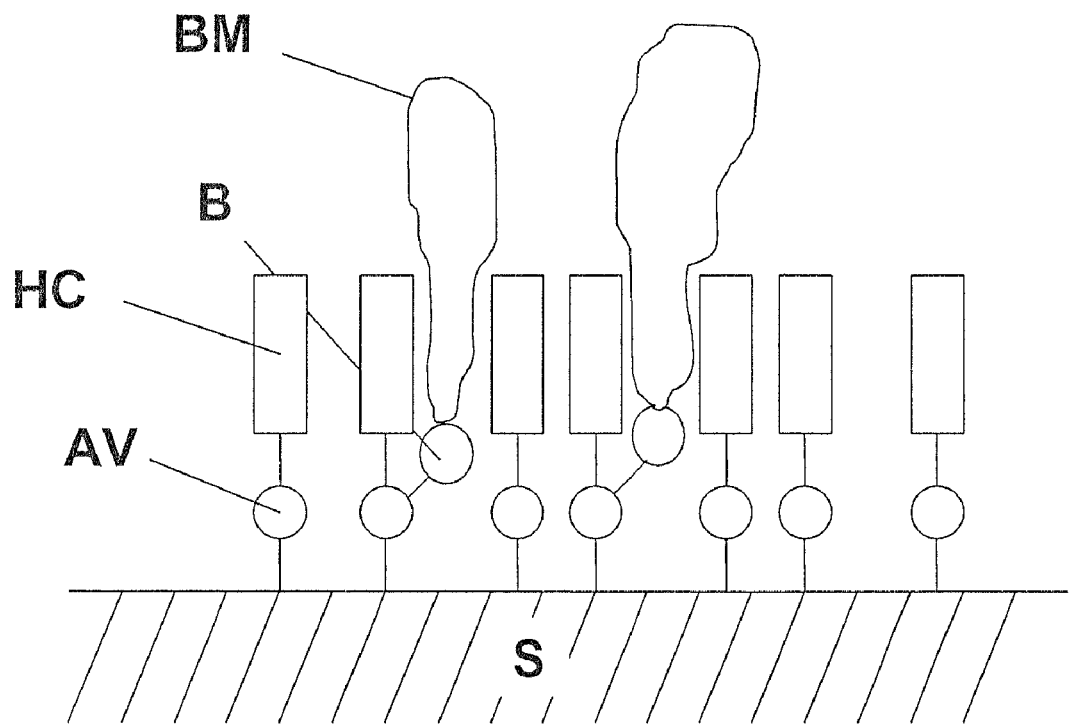
FIG. 1b illustrates an assembly according to the invention schematically.

FIG. 1b likewise schematically illustrates the general principle of the present invention, where the accessibility of the avidin (A) "inside" the heparin conjugate (HC) surface is utilized for binding a bio-molecule (BM) having a biotin (B) residue attached thereto. Thus, the bio-molecule is "anchored" to the avidin below the HC surface, via the avidin-biotin linkage, and protrudes out from the HC surface to be at the disposal for any reaction of interest.

It is possible to provide modifications of the structure disclosed in FIG. B. For example it is contemplated that more than one kind of bio-molecule is anchored to the surface by means of the method according to the invention. For example, in addition to cell capturing functionality a growth stimulating functionality could be added Thus, in its general form the invention provides an assembly, usable in several different applications, as indicated above. The assembly comprises a substrate the surface of which has an avidin layer and linked to the avidin layer a heparin layer. The heparin is attached to specific heparin binding sites of the avidin. In the heparin layer there are biotinylated biological probes anchored to the avidin molecules via specific biotin binding sites. The biomolecules preferably have sites that are reactive in some sense, i.e. have the property of being able to interact, bind to or react with some other molecule or other species, such as entire cells. Such interaction can then be monitored with suitable analytical or other techniques, for the determination of presence and/or concentration of species, or for the purpose of studying kinetics of reactions, etc. The biotinylated biomolecules or probes can be selected among a large variety of different types. Suitably they are selected from the group consisting of antibodies, fragments of antibodies, growth factors, regulators of complement, regulators of coagulation, anti-inflammatory agents, extracellular matrix proteins.

The layer of immobilised avidin on a surface may be applied in various ways. If the surface already has suitable functional groups which are capable of reacting with avidin, avidin can be attached directly thereto.

In other cases where no such functionalities are present, the surface may be modified by passive coating with e.g. various proteins such as albumin, adhesive compounds containing primary or secondary amine groups, thiol or carboxyl groups to which biotin may be covalently linked. Avidin may thereafter bind to the surface-attached biotin.

In another embodiment it would be possible to use a soluble, adhesive substance to which biotin is linked. This biotinylated substance may be used for a one-step coating procedure to introduce surface-attached biotin. Thus, avidin may then bind to the surface attached biotin.

In a further embodiment, avidin may be covalently attached to the surface modified with a polymeric substance carrying primary amine groups, using cross-linking methods well-known to the skilled person. The invention also provides a method of making an assembly as defined above. This method in a general sense is a three-step procedure essentially comprising the steps of coating a selected substrate with avidin, and then providing a layer of heparin conjugate by binding to the avidin, followed by the binding of a biotinylated bio-molecule to avidin within the surface layer, such that the bio-molecule protrudes out from the heparin surface.

Capturing of biotin-labelled molecules or cells may also be accomplished by exposing the avidin/heparin surface to blood or other bodily fluids to which biotin-labelled molecules or cells have been added. For example, let us assume that it is desired to study a specific cell type by capturing it on a chip surface for fluorescence analysis. Then an antibody targeting the cell in question can be biotinylated and added to the blood sample. The antibody will target the cell and bind thereto, and when contacted with the chip surface, the labelled cells will bind to the chip surface via the avidin-biotin link.

Another possibility is to apply the assembly according to the invention on the surface of a stent to facilitate rapid endothelialization following implantation in a patient. A biotinylated reagent suitable for capturing endothelial progenitor cells (EPC) in the blood of a patient can be injected in the patient where it binds to the EPC, and subsequently the EPC will home in at the stent where they will stimulate rapid growth of a layer of endothelial cells.

The present invention may be applied to a variety of surfaces, both biological and artificial, e.g. polymers, metals, glass, and ceramics.

In one embodiment the first step of preparing the heparin coated surface is to expose a biotinylated surface to be coated to a diluted aqueous solution of avidin, typically in the concentration interval 0.01 to 1 mg/ml, more preferably 0.01 to 0.05 mg/ml, for approximately 5 minutes or more at ambient temperature. After rinsing with water, the surface is exposed to a heparin conjugate solution according to European patent EP0658112. The heparin solution is typically of a concentration interval of 0.01 to 1 mg/ml, more preferably 0.01 to 0.05 mg/ml, in 0.15 M NaCl, and the exposure time is at least 30 minutes at ambient temperature. The surface is then carefully rinsed with pure water and the surface exhibiting the structure shown in FIG. 1a is ready for further use.

In another embodiment, wherein the substrate is not suitable for direct binding of avidin, e.g. where the substrate is of biological origin or synthetic material with low affinity for avidin, a layer of biotin is applied to the surface to be coated before coating with avidin. This can readily be made by covalent binding of e.g. NHS-Biotin (Pierce, Sweden) to primary amino groups or using chemically modified biotins to bind to other functional groups such as thiols or carboxyl groups as described in PCT/SE2006/050224. The biotinylated surface is then exposed to a dilute solution of avidin (typically in the concentration interval 0.01 to 1 mg/ml). After rinsing with water, the surface is exposed to a heparin solution according to EP0658112 (typically in a concentration interval of 0.01 to 1 mg/ml in 0.15 M NaCl) for at least 30 minutes at ambient temperature. The surface is then carefully rinsed with pure water and the heparin-surface exhibiting the structure shown in FIG. 1b is ready for further use.

In a further embodiment any type of heparin coated surface could be used for carrying out the method according to the invention, to provide an assembly according to the invention.

If the surface is cationic, a first layer of heparin (anionic) may readily be established by immersing the surface in a dilute aqueous solution of the heparin conjugate. If, on the other hand, the surface is anionic or uncharged, a cationic surface layer can readily be established by immersing the surface in a dilute aqueous solution of a suitable polymeric amine compound followed by immersing the surface in a dilute aqueous solution of the heparin conjugate.

Once a first layer of heparin has been established, the surface is immersed in a dilute aqueous solution of avidin (typically in the concentration interval 0.01 to 1 mg/ml) followed by the next step in the procedure, which is immersing the surface in a dilute aqueous solution of the heparin conjugate.

As can be seen in the schematic illustration in FIG. 1b there are enough space between the heparin conjugates HC in the heparin surface layer to expose avidin enough for it to be accessible for the binding of biotin residues present on biotinylated bio-molecules. Avidin is a relatively large molecule (60-70000) and thus the biotin-reactive sites which are distinct from the HC binding sites will be readily accessible. The accessibility can (probably) be ascribed to the very strong interaction between avidin and biotin, which is one of the strongest protein-ligand interactions that have been identified. Such addition or binding of biotinylated biomolecules to the heparin coated surface can be performed in various ways. A simple way is to expose the heparin surface to a dilute solution of the bio-molecule modified with biotin (biotinylated), whereby the biotin residue will bind to avidin by virtue of the strong affinity of the avidin-biotin pair. Another alternative is to expose the avidin/heparin surface to blood or other bodily fluids to which biotin-labelled molecules, capable of interacting with specific species in the blood, such as e.g. cells expressing specific receptors, have been added. The biotinylated part of the labelled species in the blood will then bind to the heparin surface, and form an assembly according to the invention.

As disclosed in patent application PCT/SE2006/050224 surfaces of biological origin may readily be biotinylated. The biotinylation is enabled by the fact that proteins exposed on these surfaces provide reactive groups suitable for covalent linking of biotin. It is implicated that previously disclosed methods may also be applicable to biological tissues.

Various different applications of the invention are possible, a few examples of which are mentioned below.

Components of medical apparatus can be provided with surfaces coated with the assembly according to the invention, to exhibit a specific biological functionality, such as enzymatic activity, while at the same time preventing undesired side reactions, such as thrombosis.

Capture of cells by attaching antibodies with the method according to the invention, to a heparin coated surface is very efficient.

The growth of e.g. endothelial cells can be stimulated by anchoring biotinylated growth factor in an assembly according to the invention. This is particularly useful for implants of various kinds, both based on living cells, such as those disclosed in the previously mentioned International patent application PCT/SE2006/050224. However, other implants based on other materials such as metals, polymers etc. can also be provided with a surface coating based on an assembly according to the invention.

One particular application of the present invention is to include an assembly according to the invention on a Point of Care device for diagnostic purposes. Such a device is illustrated in FIG. 2. It comprises a microchannel which is 200 μm wide, 25 μm deep and about 2 cm long, and has a total volume of 0.1 μl.

The microchannel surface is coated with an assembly according to the invention wherein the biological probe e.g. could be a biotin-CD4 antibody.

In operation a blood sample is drawn into the channel by capillarity. If CD4 cells are present in the blood they would bind to the surface in the channel, and could easily be detected by suitable methods such as confocal microscopy.

The following Examples serve to illustrate the utility of the invention, but shall not be construed to be limiting on the scope of the claims.

EXAMPLES

Example 1

Addition of Biotinylated Horse Radish Peroxidase (HRP)

The following example was designed to prove the preserved enzyme activity of HRP after biotinylation and binding to avidin.

Tubings of PVC are coated with heparin according to a well-known method (EP0658112). The tubings are divided into two groups, a first group of non-treated tubings, and a second group of tubings incubated with 0.15 M NaCl containing avidin (0.1 mg/ml) for 15 minutes at ambient temperature. After rinsing with purified water the tubings are incubated with 0.15 M NaCl containing heparin conjugate (0.05 mg/ml).

Both groups of tubings are incubated with a dilute buffer solution containing biotinylated HRP for 15 minutes at ambient temperature. The enzymatic activity in the second group is recorded as seven times higher than in the first group.

Example 2

Entrapment of CD34 Positive Progenitor Cells to a Heparin Surface in Contact with Blood Supplemented with a Biotinylated Antibody Against CD34

Peripheral blood contains hematopoetic progenitor cells expressing CD 34 at a concentration of 0.05-0.2%. A sample of citrated peripheral blood supplemented with a biotinylated antibody against CD 34 is prepared. A microscopic slide is prepared with a heparin surface according to group (a) in Example 1 and another according to group (b) in Example 1. Both slides are incubated with the blood sample at ambient temperature for 60 minutes. After careful rinsing, the slides are incubated with a fluorescent antibody against CD 133 and examined by confocal microscopy. Slide (b) will display a number of positive cells but no positive cells will be detected on slide (a).

Example 3

Improved Growth of Endothelial Cells on a Heparin Surface Supplemented with Biotinylated Growth Factor (VEGF)

Cell culture wells are modified with a heparin surface according to group (b) in Example 1. One row of wells are left without further treatment and the next row is incubated with a buffer solution containing biotinylated VEGF for fifteen minutes at ambient temperature and then carefully rinsed with saline. The two rows are then incubated with culture medium containing endothelial cells. Examination by confocal microscopy reveals improved outgrowth of endothelial cells in the wells that had been supplemented with biotinylated VEGF Example 4

Less Complement Activation Induced by Islets of Langerhans Modified with a Surface Coating of Heparin Supplemented by Biotinylated Factor H Isolated islets of Langerhans are modified with a heparin coating according to patent application PCT/SE2006/050224, which includes sequential treatment with biotin, avidin and heparin conjugate according to European patent EP0658112. One group of islets is further incubated with medium containing biotinylated factor H (a complement regulatory protein). The islets are then exposed to whole blood using a test method previously described (Bennet et. al., Diabetes, 1999, 48, 1907-14).The degree of complement activation is considerably lower in the group supplemented with complement factor H.

Example 5

Cell Capturing by a Diagnostic Sensor

Figure 2A:
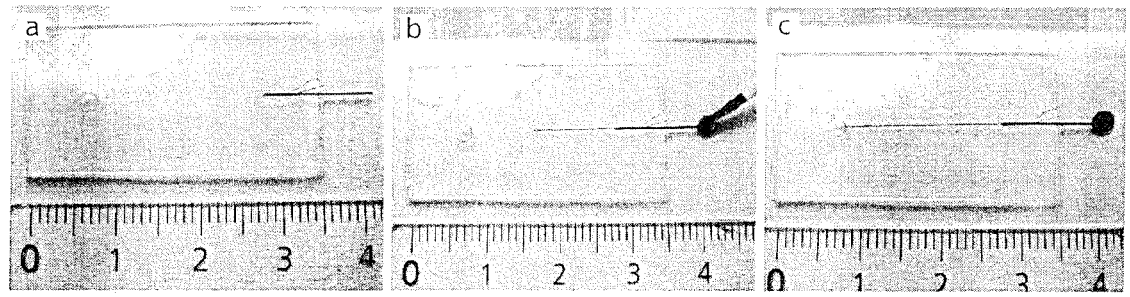
FIG. 2 shows a device implementing the invention.
Figure 2B:
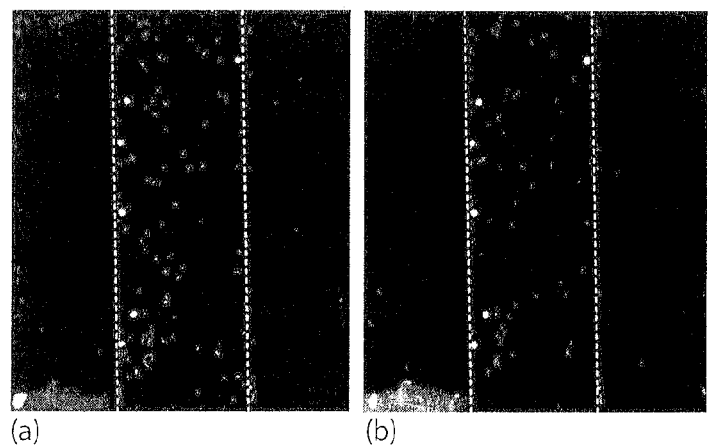

A PDMS sensor chip, ready for cell capturing, FIG. 2a. By holding a droplet of blood against the capillary ending, the empty microchannel was immediately filled with blood, due to its hydrophilic surface, FIGS. 2b-c.

A biosensor channel was prepared with avidin followed by the heparin conjugate. In this specific experiment, the biotin-CD4 antibodies were added to blood to target CD4 positive cells. A blood sample was then exposed to the sensor channel as showed above. Examination by fluorescence microscopy revealed that six cells were captured by the avidin/heparin surface. FIGS. 3a and 3b shows a HOECHST fluorescence image (a), and a CD3-FITC fluorescence image (b), respectively, of the channel. The example shows that the avidin/heparin surface is capable of capturing biotin-labelled cells.

The invention claimed is:

1. A molecular assembly on a substrate, comprising
   a substrate with a surface capable of binding avidin,
   a layer of avidin directly linked to the substrate surface;
   a heparin layer linked to avidin in the avidin layer,
   characterized by
   one or more different types of biotinylated biological probes directly anchored to the avidin, said biological probes extending out from the heparin layer and exposing a reactive site of interest.

2. The assembly according to claim 1 wherein the substrate comprises a reagent covalently linked to the substrate surface, the avidin layer comprises avidin linked to the reagent, and the heparin layer comprises heparin reagent linked to the avidin layer.

3. The assembly according to claim 1 wherein the reagent covalently linked to the substrate surface is selected from the group consisting of biotin, heparin or a polymeric substance carrying primary amine groups.

4. The assembly according to claim 1 wherein the biotinylated biological probes are biotinylated biomolecules.

5. The assembly according to claim 4 wherein the biotinylated biomolecules are selected from the group consisting of antibodies, fragments of antibodies, growth factors, regulators of complement, regulators of coagulation, anti-inflammatory agents, and extracellular matrix proteins.

6. The assembly according to claim 1, wherein the substrate is of artificial or biological origin.

7. An in vitro method of providing an molecular assembly on a substrate comprising the following steps;
   (a) directly linking avidin to a surface capable of binding avidin,
   (b) linking a heparin conjugate to the avidin treated surface to form a layer of heparin thereon, and
   (c) directly linking biotinylated biological probes to the avidin through the layer of heparin such that the probes extend out from the surface.

8. The method according to claim 7 wherein the substrate surface comprises a surface coated with species selected from heparin, biotin, or a polymeric substance carrying primary amine groups.

9. The method according to claim 7, wherein the substrate is of artificial or biological origin.

10. The method according to claim 7, wherein the avidin concentration used in the avidin linking step is in the range of 0.01-1 mg/ml, preferably 0.01-0.05 mg/ml.

11. The method according to claim 7, wherein the heparin reagent concentration used in the heparin linking step is in the range of 0.01-1 mg/ml, preferably 0.01-0.05 mg/ml.

12. The method according to claim 7, wherein the biotinylated biological probes are selected from a group consisting of antibodies, fragments of antibodies, growth factors, regulators of complement, regulators of coagulation, anti-inflammatory agents, extracellular matrix proteins.

13. The method according to claim 7, wherein the biotinylated biological probes are biotinylated biomolecules.

14. Implant structure comprising an assembly according to claim 1.

15. A biosensor device comprising a measurement region the surface of which comprises an assembly according to claim 1.

16. The biosensor according to claim 15, wherein the measurement region is a reaction cell.

17. An assembly comprising a substrate with a surface capable of binding avidin, an avidin layer and a heparin layer, having biotinylated biological probes directly anchored to the avidin and extending out from the heparin layer and exposing a reactive site of interest.

* * * * *